United States Patent [19]

Baldwin et al.

[11] Patent Number: 4,602,093

[45] Date of Patent: Jul. 22, 1986

[54] NOVEL SUBSTITUTED IMIDAZOLES, THEIR PREPARATION AND USE

[75] Inventors: John J. Baldwin, Gwynedd Valley; Gerald S. Ponticello, Lansdale; Marcia E. Christy, Perkasie, all of Pa.

[73] Assignee: Merck & Co., Inc., Rahway, N.J.

[21] Appl. No.: 578,145

[22] Filed: Feb. 8, 1984

[51] Int. Cl.$^4$ .................. C07D 409/10; C07D 233/64
[52] U.S. Cl. ..................................... 548/336; 544/238; 544/295; 544/296; 544/328; 544/331; 544/357; 544/370; 546/193; 546/194; 546/256; 546/210; 546/278; 548/337; 548/342; 548/343
[58] Field of Search ............... 514/400; 548/342, 343, 548/336, 337; 546/193, 194, 210, 256, 278; 544/238, 370, 295, 296, 328, 331, 357

[56] References Cited

U.S. PATENT DOCUMENTS

| | | | |
|---|---|---|---|
| 4,125,530 | 11/1978 | Baldwin | 546/278 |
| 4,134,983 | 1/1979 | Baldwin | 548/342 |
| 4,199,580 | 4/1980 | Baldwin | 548/342 |
| 4,324,792 | 4/1982 | Bradshaw | 548/342 |
| 4,355,040 | 10/1982 | Furukawa | 548/336 |
| 4,358,571 | 11/1982 | Kaufman | 548/342 |
| 4,440,774 | 4/1984 | Baldwin | 514/400 |

OTHER PUBLICATIONS

P. J. Machin, et al., J. Med. Chem., 27, 503-509 (1984).

*Primary Examiner*—C. Warren Ivy
*Attorney, Agent, or Firm*—Alice O. Robertson; Salvatore C. Mitri; Michael C. Sudol

[57] ABSTRACT

Novel substituted imidazoles and methods for their preparation are disclosed. These imidazoles, and their salts, exhibit cardioselective β-adrenergic blocking activity, and are useful as antihypertensive agents, cardioprotective agents, antiarrythmic agents, antianginal agents with reduced side effects; e.g., they are devoid of intrinsic sympathomimetic activity.

12 Claims, No Drawings

NOVEL SUBSTITUTED IMIDAZOLES, THEIR PREPARATION AND USE

BACKGROUND OF THE INVENTION

The present invention involves novel imidazoles which have cardioselective β-adrenergic blocking activity and which are useful as antihypertensive agents, cardioprotective agents, antiarrythmic agents, antianginal agents with reduced side effects; e.g., they are devoid of intrinsic sympathomimetic activity (IsA).

A class of pharmaceutical agents, known as β-adrenergic blocking agents, are available and are known to affect cardiac, vascular and pulmonary functions and are mild antihypertensives. Specifically, these agents have the capability of reducing heart rate, without counteracting vasodepression or suppressing bronchodilation. β-adrenergic blocking agents, their chemical structure and activity, are generally disclosed in "Clinical Pharmacology and Therapeutics" 10, 292-306 (1969). Various β-adrenergic blocking agents are also described in such patents as, for example, U.S. Pat. Nos. 3,048,387; 3,337,628; 3,655,663; 3,794,650; 3,832,470; 3,836,666; 3,850,945; 3,850,946; 3,850,947; 3,852,291 and British Pat. No. 1,194,548.

U.S. Pat. Nos. 4,134,983 and 4,199,580 disclose a class of substituted imidazoles which have β-adrenergic blocking activity. While such compounds are effective, their use results in undesirable side affects such as bronchial constriction, muscular fatigue and cold extremities.

SUMMARY OF THE INVENTION

A novel class of substituted imidazoles has been discovered which exhibit cardioselective β-adrenergic blocking activity and are devoid of partial β-agonism i.e., intrinsic sympathomimetic activity (ISA). This new class of substituted imidazoles may also be free from the undesirable side affects associated with the use of the substituted imidazoles disclosed in U.S. Pat. Nos. 4,134,983 and 4,199,580 identified hereinabove. By virtue of their β-blocking activity, the novel imidazoles of the invention also exhibit antihypertensive, cardioprotective, antiarrythmic and antianginal activity. In addition, these novel imidazoles are devoid of undesirable side-effects; e.g., they are devoid of intrinsic sympathomimetic activity (ISA).

DESCRIPTION OF PREFERRED EMBODIMENTS

The compounds of the present invention are represented by the general formula:

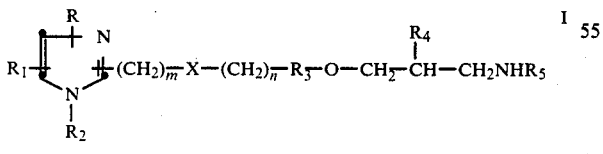

wherein
R and $R_1$ are independently hydrogen;
$C_1-C_8$ linear or branched alkyl; substituted $C_1-C_8$ linear or branched alkyl having 1-3 substituents selected from halo (F, Br, Cl), $C_1-C_8$alkoxy, amino, mono- or di-substituted amino wherein the substituent is $C_1-C_8$ linear or branched alkyl, aryl of $C_6$ or $C_{10}$, aralkyl wherein the aryl is $C_6$ or $C_{10}$ and the alkyl group is $C_1-C_3$, or which, together with the N atom, forms a 5- or 6-membered ring wherein the 6-membered ring can contain a hetero group selected from O, S, NH or N-lower $C_1-C_8$ alkyl;

aryl of $C_6$ or $C_{10}$;
substituted aryl of $C_6$ or $C_{10}$ having 1-5 substituents selected from halo (F, Br, Cl), $C_1-C_8$ linear or branched alkyl, or $C_1-C_8$alkoxy;
heteroaryl groups having 5 ring atoms one of which is an O, N-lower $C_1-C_8$ alkyl or S heteroatoms;
heteroaryl groups having 6-ring atoms containing 1-2N heteroatoms;
halo (F, Br, Cl);
cyano;
carboxy;
carboalkoxy wherein the alkyl group has up to 8 carbon atoms;
carbamoyl;
mono- or di-substituted carbamoyl wherein the substituent is $C_1-C_8$ linear or branched alkyl or which, together with the N atom forms a 5- or 6-membered ring wherein the 6-membered ring can contain a hetero group selected from O, S, NH or N-lower $C_1-C_8$alkyl;

wherein Ra is H or $C_1-C_8$alkyl;
$R_2$ is hydrogen;
$C_1-C_8$ linear or branched alkyl;
$R_3$ is aryl or substituted aryl of $C_6$ to $C_{10}$ including tetralin and indane having 1-2 substituents selected from halo (F, Br, Cl), $C_1-C_8$ alkoxy, alkenyloxy having up to 8 carbon atoms, $C_1-C_8$ linear or branched alkyl, $C_2-C_8$ alkenyl, cyano,

wherein Ra is as defined above;
$R_4$ is hydroxy;

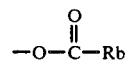

wherein Rb is $C_1-C_8$ alkyl or aryl of $C_6$ or $C_{10}$;
$R_5$ is $C_1-C_8$ linear or branched alkyl;
$C_3-C_6$cycloalkyl;
substituted $C_1-C_8$alkyl having 1-2 substituents selected from $C_1-C_8$alkoxy, thioalkyl of $C_1-C_8$, ureido, substituted ureido having the formula:

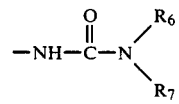

wherein $R_6$ and $R_7$ can independently be hydrogen, $C_1-C_8$ alkyl optionally substituted with hydroxy, $C_1-C_8$ alkoxy;
unsubstituted or substituted aryl of $C_6$ or $C_{10}$ having 1-2 substituents selected from halo, lower $C_1-C_4$ alkoxy, and $C_1-C_4$ alkyl, or $R_6$ and $R_7$ together with the N atom can be joined to form a 6-membered heterocyclic ring containing an additional O, S, NH, or N-lower-$C_1$-$C_8$ alkyl heteroatom;

unsubstituted or substituted aralkyl wherein the alkyl group is linear or branched $C_1$-$C_8$ and the aryl is $C_6$ having 1-2 substituents selected from $C_1$-$C_8$ alkoxy, hydroxy, halo (F, Br, Cl), $C_1$-$C_8$alkyl;

heteroaralkyl having 6 ring atoms containing 1-2N heteroatoms and the alkyl is $C_1$-$C_8$;

X is $CH_2$, O or S;

m and n are independently 0, 1, 2 or 3;

provided that when m and n are each zero, X is $CH_2$; and, the pharmacologically acceptable acid addition salts thereof.

Compounds of particular interest have the formulae:

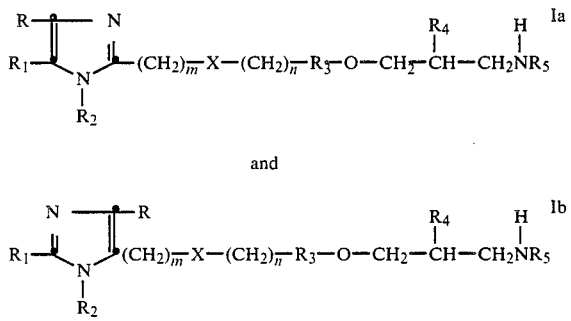

wherein $R$-$R_5$, X, m and n are as defined above.

Examples of suitable R and $R_1$ aryl groups include pentafluorophenyl, 3,4-dichlorophenyl, 4-bromophenyl, 4-ethoxy-3-chlorophenyl, 4-methyl-2,3-dichlorophenyl, 2-propylphenyl, 4-isopropylphenyl, phenyl, 2-methoxy-4-methylphenyl, 2,5-dimethoxy-3,4-dimethylphenyl, and the like.

Illustrative R and $R_1$ 5-membered heteroaryl groups include 2-furyl, 3-furyl, 2-thienyl, 3-thienyl, N-methyl-2-pyrrolyl, and the like.

Exemplary R and $R_1$ 6-membered heteroaryl groups include 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl and the like.

With respect to the $R_3$ aryl groups, the imidazole alkyl group and the hydroxy propoxy amine group are situated ortho, meta or para to each other. Accordingly, suitable $R_3$ aryl groups include 2,3-dichloro-1,4-phenylene, 3-chloro-1,4-phenylene, 1,4-naphthalene, 3-allyloxy-1,4-phenylene, 3-allyl-1,4-phenylene, 3-cyano-1,4-phenylene, 3-acetyl-1,4-phenylene, 5,6,7,8-tetrahydro-1,4-naphthalene, 5,6-dihydro-1,4-indane, 3-methyl-1,4-phenylene, 2,3-dimethyl-1,4-phenylene, 4-ethyl-1,3-phenylene, 4-bromo-1,3-phenylene, 5-chloro-1,2-phenylene, 1-pentanone-1-(2,5-phenylene), 4-n-butoxy-1,3-phenylene, 3-fluoro-1,4-phenylene, and the like.

Illustrative aryl groups in the $R_5$ aralkyl moiety include 3,4-dimethoxyphenyl, 3,4-di-n-butoxyphenyl, 3,4-methylenedioxyphenyl, 3-hydroxy-4-methoxyphenyl, 3-methoxy-4-hydroxyphenyl, 3,4-dihydroxyphenyl, 3-hydroxyphenyl, 3-methoxyphenyl, 4-hydroxyphenyl, 4-methoxyphenyl, 2-ethoxyphenyl, 2-hydroxyphenyl, 3,4-dichlorophenyl, 3,5-dibromophenyl, 3-hydroxy-4-chlorophenyl, 4-chloro-3-hydroxyphenyl, 4-fluorophenyl, 4-hexyloxyphenyl, 3-methylphenyl, 3,4-dimethylphenyl, and the like.

The 6-membered heteroaryl groups for the $R_5$ heteroaralkyl groups include the same 6-membered heteroaryl groups described above for R and $R_1$.

Illustrative $R_6$ and $R_7$ groups include methyl, ethyl, n-butyl, hydroxyethyl, methoxybutyl, phenyl, benzyl, and the like and when $R_6$ and $R_7$ are joined together with the N-atom, they form such hetero rings as

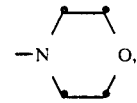

and the like.

Preferred are those compounds of Formula I wherein:

R and $R_1$ are independently:
hydrogen;
$C_{1-8}$ linear or branched alkyl;
halo;
heteroaryl groups having 5-ring atoms, one of which is an O, N—$C_1$-$C_8$-loweralkyl, or S hetero group;
carboalkoxy wherein the alkyl group has up to 8 carbon atoms;
$CF_3$;
carbamoyl
cyano;

wherein $R_a$ is hydrogen or $C_1$-$C_8$ alkyl;
unsubstituted or substituted aryl of $C_6$ having 1-5 substituents selected from halo, $C_1$-$C_8$ linear or branched alkyl, or $C_1$-$C_8$ alkoxy; heteroaryl groups having 6-ring atoms containing 1-2N heteroatoms;

$R_2$ is hydrogen;
$C_1$-$C_8$ linear or branched alkyl;

$R_3$ is unsubstituted or substituted aryl of $C_6$ or $C_{10}$ having 1-2 substituents selected from halo, $C_1$-$C_8$ alkoxy, alkenyloxy having up to 8 carbon atoms; $C_1$-$C_8$ linear or branched alkyl, cyano,

wherein $R_a$ is as defined above;
$R_4$ is hydroxy;
$R_5$ is $C_3$-$C_5$ cycloalkyl;
$C_1$-$C_8$ linear or branched alkyl;
unsubstituted or substituted aralkyl wherein the alkyl is linear or branched $C_1$-$C_8$ and the aryl is $C_6$ or $C_{10}$ having 1-2 substituents selected from $C_1$-$C_8$ alkoxy, hydroxy, halo, $C_1$-$C_8$ alkyl; heteroaryl having 6-ring atoms containing 1-2N heteroatoms;
X is oxygen or $CH_2$; and,
m and n are independently 0-2 provided that at least one of m or n is 1.

More preferred are compounds of Formula I wherein:
R and $R_1$ are independently
hydrogen;
$C_1$-$C_8$ linear or branched alkyl;
halo;

heteroaryl groups having 5-ring atoms, one of which is an O or S heteroatom;
carboalkoxy wherein the alkyl group has up to 8 carbon atoms;
$CF_3$;

wherein $R_a$ is $C_1$-$C_3$ alkyl;
$R_2$ is hydrogen;
$R_3$ is 1,4-phenylene;
$R_4$ is hydroxy;
$R_5$ is $C_3$-$C_5$ cycloalkyl; p1 $C_1$-$C_8$ linear or branched alkyl;
unsubstituted or substituted aralkyl wherein the alkyl is linear or branched $C_1$-$C_8$ and the aryl is $C_6$ having 1-2 $C_1$-$C_8$ alkoxy substituents;
X is $CH_2$; and,
m and n are independently zero or 1.

The compounds of the present invention include all the optical isomer forms. In other words, the compounds include mixtures containing the optical isomers such as racemic mixtures, diastereomeric mixtures, as well as the individual optical isomers.

The compounds of the present invention also include the N-oxides and the non-toxic pharmacologically acceptable acid addition salts of the present imidazoles. The acid addition salts are prepared by treating the compounds of the invention with an appropriate amount of a suitable organic or inorganic acid. Examples of useful organic acids are carboxylic acids such as maleic acid, tartaric acid, acetic acid, pamoic acid, oxalic acid, propionic acid, salicylic acid, succinic acid, citric acid, malic acid, isethionic acid, and the like; useful inorganic acids are hydrohalo acids such as HCl, HBr and HI, sulfuric acid, $H_3PO_4$, and the like.

Compounds of the present invention may be prepared by any convenient method; however, the methods actually utilized will depend upon the R-$R_5$ substituents as well as X, m and n. In the methods described below the R-$R_5$ groups, X, m and n, are as defined above unless otherwise indicated. Also, unless otherwise indicated, the starting materials employed are known in the literature, are commercially available, or can be prepared by methods known to those skilled in the art.

METHOD A

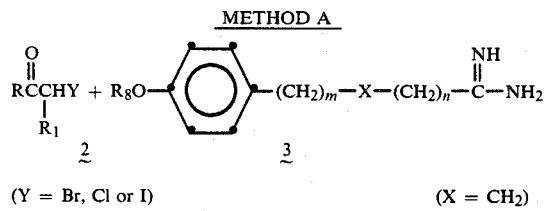

(Y = Br, Cl or I)    (X = $CH_2$)

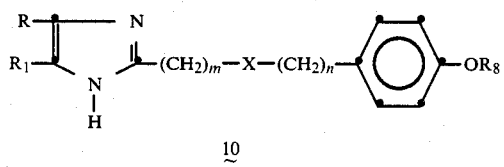

As shown in Method A, α-haloketone 2 is reacted with amidine 3 in a suitable solvent such as chloroform, acetonitrile, tetrahydrofuran (THF), acetone, methylene chloride, and the like, preferably chloroform, at a temperature of from about 0° C. to the reflux temperature of the solvent, preferably at ambient temperature, over a period of about 1-48 hours to obtain imidazole 10 wherein $R_8$ is a suitable protecting group such as methyl, benzyl, and the like. In this Method, amidine 3 is prepared from a nitrile using standard procedures described in the literature.

METHOD B

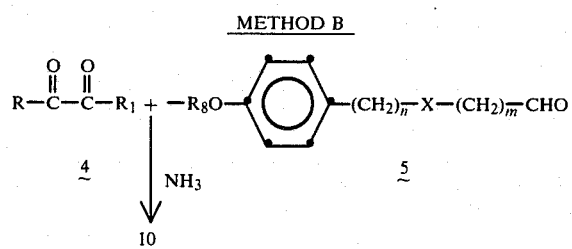

In Method B, glyoxal 4 is reacted with aldehyde 5 using a suitable alcohol solvent such as methanol, ethanol, and the like, or a suitable solvent such as THF, acetonitrile, dimethylformamide (DMF), and the like, preferably methanol to obtain imidazole 10 wherein $R_8$ is as defined for Method A.

METHOD C

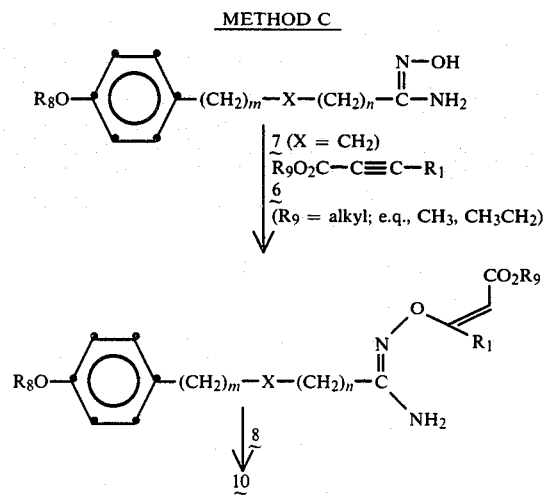

To obtain imidazole 10 by Method C, amidoxime 7 (prepared from the corresponding nitrile by reaction with hydroxylamine) is treated with a substituted propiolate ester 6 in an alcohol solvent (e.g., $CH_3OH$, EtOH) or a suitable solvent such as acetonitrile, THF, acetone, DMF, and the like, preferably an alcohol, to obtain olefin 8. In olefin 8, when $R_1$=H, there is obtained a mixture of cis and trans isomers and when $R_1$=alkyl or aryl, there is obtained a mixture of E and Z isomers. Olefin 8 is then treated in a solvent such as DMF, dimethylsulfoxide (DMSO), diphenylether, xylene, and the like, at temperatures of about 0° C. to the reflux temperature of the solvent, preferably about 190° C. in diphenylether over a period of about ½ to 2 hours to yield imidazole 10 ($R_1$=H, alkyl, aryl; $R_2$=$CO_2R_9$).

METHOD D

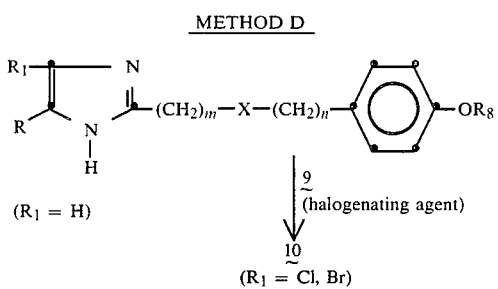

($R_1$ = H)

9 (halogenating agent)

10 ($R_1$ = Cl, Br)

In Method D, imidazole 9 ($R_1$=H and $R_8$ is as defined in Method A) is treated with a halogenating agent such as $Br_2$, $Cl_2$, N-chlorosuccinimide, N-bromosuccinimide, potassium chlorate, sodium hypochlorite, cyanogen chloride, cyanogen bromide, pyridine perbromide, and the like, in a solvent such as chloroform, acetonitrile, DMF, THF, water, and the like at 0° C. to the reflux temperature of the solvent over a period of about 15 minutes to 24 hours to obtain imidazole 10.

METHOD E

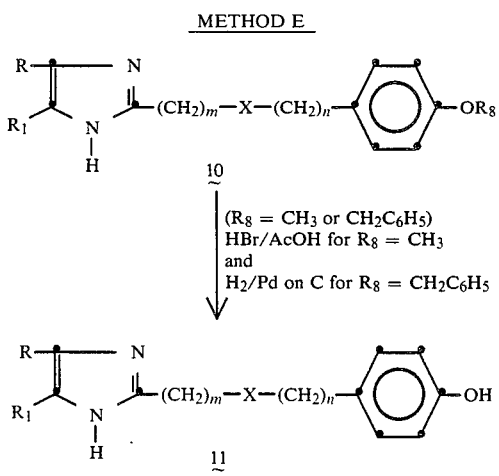

10

($R_8$ = $CH_3$ or $CH_2C_6H_5$)
HBr/AcOH for $R_8$ = $CH_3$
and
$H_2$/Pd on C for $R_8$ = $CH_2C_6H_5$

11

As shown in Method E, imidazole 10 ($R_8$=$CH_3$) is treated with any ether cleaving reagent such as 48% HBr in acetic acid, pyridine-HCl, $AlCl_3/C_6H_6$, and $BBr_3/CH_2Cl_2$ at 0° to the reflux temperature of the solvent for about 1-24 hours to obtain imidazole phenol 11 (X=$CH_2$). Imidazole 10 ($R_8$=$CH_2C_6H_5$) is treated with a suitable solvent such as an alcohol ($CH_3OH$, EtOH, and the like) or acetic acid at ambient temperature for a period of about 15 minutes to about 15 hours in the presence of a suitable catalyst such as 10% Pd on carbon, platinum oxide, and the like, at a pressure of up to about 60 psi to afford imidazole 11 (X=$CH_2$ or X=O when m and n are >1).

METHOD F

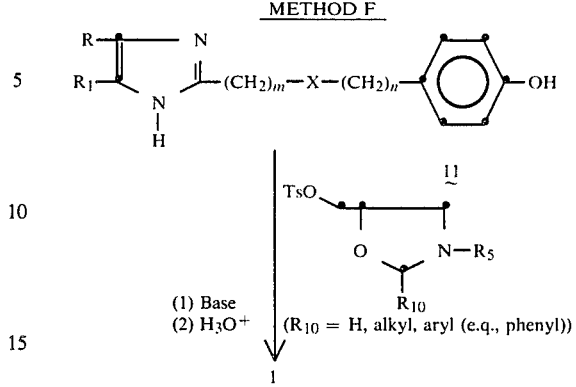

(1) Base
(2) $H_3O^+$ ($R_{10}$ = H, alkyl, aryl (e.q., phenyl))

1

For Method F, imidazole phenol 11 is prepared as described in Method E above and is then reacted with the oxazolidine tosylate or any other suitable leaving group such as mesylate, triflate, or iodide, and a base such as sodium hydride, sodium methoxide, sodium hydroxide, potassium t-butoxide, and the like, preferably sodium hydride, in an appropriate solvent such as DMSO, DMF, toluene, methanol, water, and the like, preferably DMF, at 0° C. to the reflux temperature of the solvent over a period of about 1-48 hours, preferably 110° for 18 hours, to obtain an oxazolidine intermediate.

The oxazolidine intermediate is then subjected to acid hydrolysis using such acids as aqueous HCl, $H_2SO_4$, acetic acid, and the like, at 0° to the reflux temperature of the solvent for about 15 minutes to 15 hours, preferably in 1N HCl for 15 minutes at 100°, to obtain imidazole 1.

METHOD G

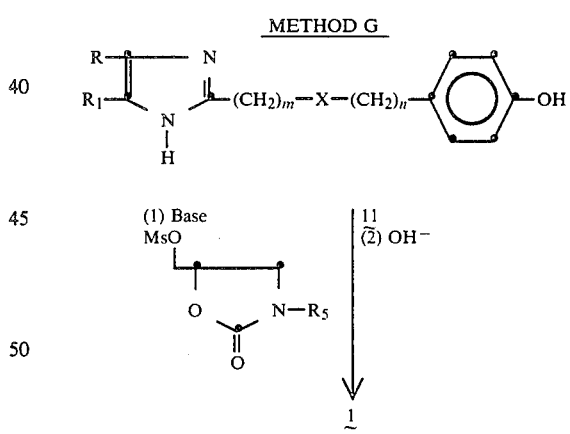

(1) Base
MsO 11
(2) $OH^-$

1

In Method G, imidazole phenol 11 is first reacted with a base and the oxazolidone mesylate [prepared according to the methods described in Canadian Pat. No. 965,787] or any other suitable leaving group such as tosylate, triflate or iodide, preferably using NaH as base, DMSO as solvent at 60° C. for 2 hours, followed by treatment with an aqueous base such as sodium hydroxide, potassium hydroxide, and the like, at a strength of 1-40% in an appropriate solvent such as methanol, ethanol, acetone, THF, and the like (preferably 10% NaOH—EtOH, 1:1), at the reflux temperature of the solvent over a period of about 15 minutes to 24 hours, preferably for 2 hours at 100° C., to afford imidazole 1.

METHOD H

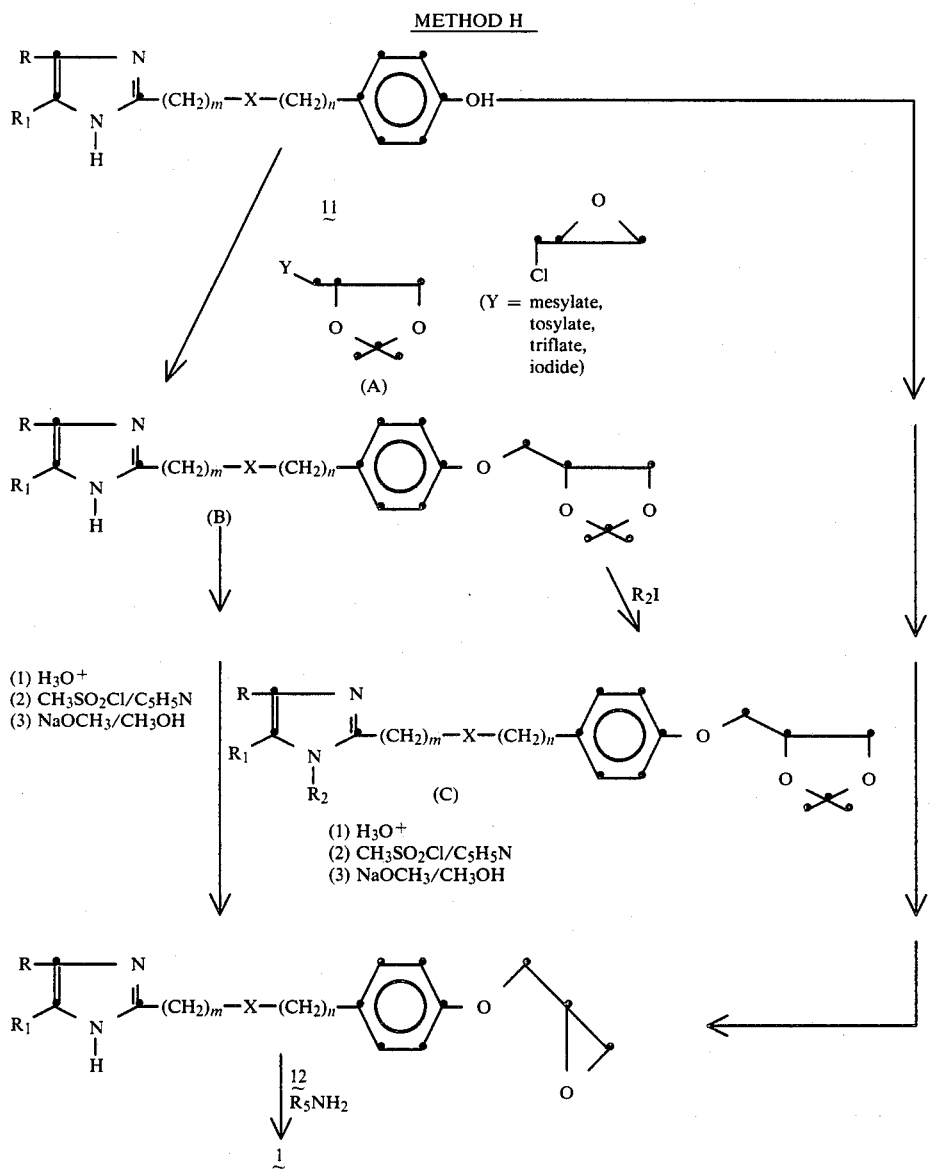

As shown in Method H, epoxide 12 can be prepared by reaction of phenol 11 with epichlorohydrin in an aqueous base. Alternatively, phenol 11 can be reacted with acetonide (A) containing a suitable leaving group such as mesylate, tosylate, triflate or iodide in a suitable solvent as described in Method F above to provide compound (B). Reaction of compound (B) with an alkylating agent ($R_2I$) provides type (C) compounds where $R_2$ is an alkyl group. Hydrolysis of compound (B) in a mineral acid as described in Method E, followed by mesylation of the primary alcohol and subsequent treatment with $NaOCH_3$ yields epoxide 12. Treatment of epoxide 12 with an amine ($R_5NH_2$) in an appropriate solvent (THF, methylene chloride, methanol, isopropyl alcohol; preferably a mixture of methylene chloride and methanol) at about 0° C. to reflux temperature of the solvent for about 1 to 48 hours affords imidazole 1.

When compound (C) is used in place of compound (B), imidazoles 1 are obtained where $R_2$ is an alkyl group.

METHOD I

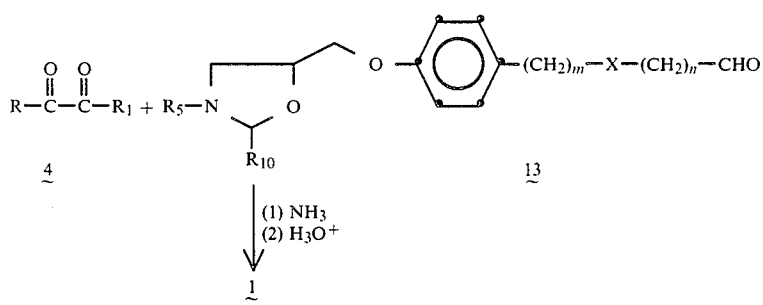

In Method I, glyoxal 4 is reacted with oxazolidine protected aldehyde 13 under the same conditions as described in Method B above, and is then subjected to acid hydrolysis as described in Method F above to obtain imidazole 1.

METHOD J

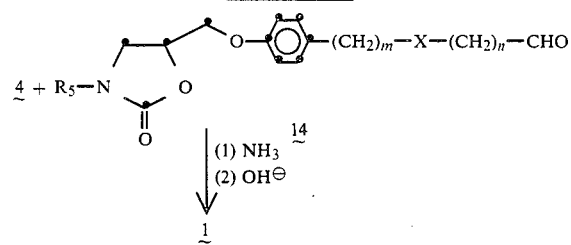

For Method J, the same procedure is followed as described in Method B for reacting glyoxal 4 with oxazolidine protected aldehyde 14 followed by base hydrolysis as described in Method G to obtain imidazole 1.

METHOD K

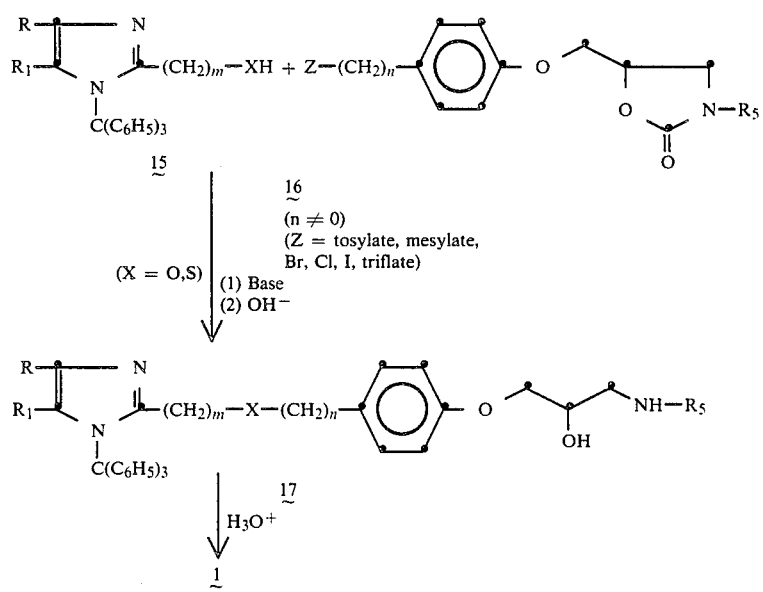

Following the same procedures as described in Method G, imidazole 17 is prepared from the reaction of imidazole 15 and oxazolidone 16 after base hydrolysis.

Imidazole 17 is then treated in an appropriate solvent such as dilute mineral acid (HCl, $H_2SO_4$, $H_3PO_4$ and the like) or alcohol/acetic acid mixtures, preferably in $CH_3OH$—AcOH, at 0° C. to the reflux temperature of the solvent, preferably 2 hours in refluxing $CH_3OH$, to yield imidazole 1.

METHOD L

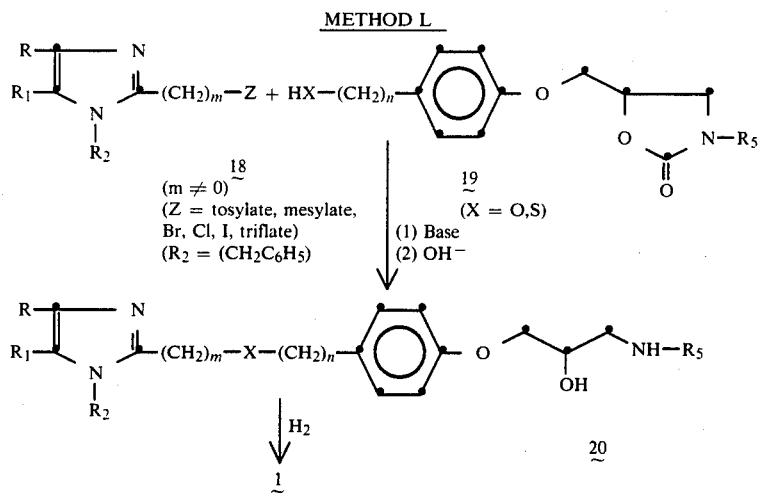

Following the same procedures as described in Method G, imidazole 18 and oxazolidone 19 yielded imidazole 20 which was then treated as described in Method E ($R_8=CH_2C_6H_5$) to remove the $CH_2C_6H_5$ protecting group and afford imidazole 1.

In Methods K and L, compounds 16 and 19 can also be prepared as the corresponding oxazolidines. The resulting compounds can then be subjected to acid hydrolysis to cleave the protected oxazolidine ring to afford imidazole 1.

The Methods illustrated hereinabove permit preparation of single optical isomers and/or racemates or diastereomers. In the foregoing Methods, the oxazolidines were prepared according to the processes disclosed and described in U.S. Pat. Nos. 3,892,744 and 4,051,144.

The compounds of the present invention are active as cardioselective β-adrenergic blocking agents, are useful as antihypertensive, cardioprotective, antiarrythmic, and antianginal agents and are devoid of intrinsic sympathomimetic activity (ISA).

The β-adrenergic blocking activity (β-blockade) of the present compounds was determined by measuring the ability of representative compounds to block isoproterenol induced tachycardia without counteracting vasodepression or suppressing bronchodilatation in animals. Administration of the imidazoles of the present invention (generally as an acid addition salt) was used for this evaluation.

Representative compounds of Formula I which exhibited β-adrenergic blocking and antihypertensive activity are listed below:

(a) (S)-2-{p-[3-(3,4-dimethoxyphenylethylamino)-2-hydroxypropoxy]phenylmethyl}-4-methylimidazole;

(b) (S)-2-[p-(3-t-butylamino-2-hydroxypropoxy)phenylmethyl]-4-(2-thienyl)imidazole;

(c) (S)-2-[p-(3-t-butylamino-2-hydroxypropoxy)phenylmethyl]-4-methylimidazole;

(d) (S)-1-(4-bromoimidazol-2-yl)-2-{p-[3-(3,4-dimethoxy-phenylethylamino)-2-hydroxypropoxy]-phenyl}ethane;

(e) (S)-1-[4-(2-thienyl)imidazol-2-yl]-2-{p-[3-(3,4-dimethoxyphenylethylamino)-2-hydroxypropoxy]-phenyl}ethane;

(f) (S)-4-bromo-2-[p-(3-isopropylamino-2-hydroxypropoxy)phenylmethyl]imidazole;

(g) (S)-2-{p-[3-(3,4-dimethoxyphenethylamino)-2-hydroxypropoxy]phenylmethyl}-4-acetylimidazole;

(h) (S)-3-[3,4-dimethoxyphenylethylamino]-2-hydroxy-1-[4-[2-imidazolylmethoxymethyl]phenoxy]propane;

(i) (S)-3-(3,4-dimethoxyphenylethylamino)-2-hydroxy-1-[4-(2-imidazolylmethoxy)phenoxy]propane.

The β-adrenergic blocking effectiveness of the compounds of the present invention indicates that they are also useful to treat humans suffering from undesirable conditions such as angina pectoris or certain arrhythmias which are known to be amenable to treatment with β-adrenergic blocking agents. Thus, the compounds of the invention are useful as antihypertensive, cardioprotective, antiarrythmic, and antianginal agents with reduced side effects; e.g., they are devoid of ISA. Furthermore, the cardioselective nature of the compounds of the present invention offers the advantage of limiting blockade to only the $β_1$ receptors; i.e., those which control heart rate. Thus, these β-blocking agents are also useful to control tachycardia which may be drug induced (as by isoproterenol) or brought about by physiological conditions, reduce intraocular pressure in the treatment of glaucoma, and inhibit renal renin secretion.

For use as antihypertensive and/or β-adrenergic blocking agents, the present compounds can be administered orally or parenterally; i.e., intravenously, interperitoneally, etc. and in any suitable dosage form. The compounds may be offered in a form (a) for oral administration; e.g., as tablets, in combination with other compounding ingredients customarily used such as talc, vegetable oils, polyols, benzyl alcohols, gums, gelatin, starches and other carriers; dissolved or dispersed or emulsified in a suitable liquid carrier; in capsules or encapsulated in a suitable encapsulating material; or (b) for parenteral administration; e.g., dissolved or dispersed in a suitable liquid carrier or emulsified or (c) for transdermal application.

It is often advantageous to administer compounds of this invention in combination with angiotensin converting enzyme inhibitors and/or antihypertensives and/or diuretics. For example, the compounds of this invention can be given in combination with such compounds as enalapril, hydrochlorothiazide, hydralazine hydrochloride, methyldopa, and the like, as well as admixtures and combinations thereof.

The ratio of active compound of the invention to compounding ingredients; i.e., carrier, diluent, etc., and/or other combination compounds will vary as the dosage form requires. Whatever dosage form is used, the amount of compound of the present invention administered should be sufficient to effect (a) a reduction in blood pressure of the patient suffering from hypertension and/or (b) desirable level of β-blockade in the patient. Generally, doses of the present compounds can be administered in amounts of from about 1 mg to about 1 g and preferably from about 5 to about 500 mg per day. Dosage may be single or multiple depending on the daily total required and the unit dosage.

Following are examples illustrating representative pharmaceutical formulations containing imidazoles of the present invention. Conventional techniques are used to prepare these formulations

| INGREDIENT | AMOUNT (Mg.) |
| --- | --- |
| TABLET FORMULATION | |
| (S)—2-{p-[3-(3,4-dimethyoxyphenethyl-amino)-2-hydroxypropoxy]-phenylmethyl}-4-acetylimidazole | 40.0 |
| calcium phosphate | 120.0 |
| lactose | 50.0 |
| starch | 23.5 |
| magnesium stearate | 1.5 |
| CAPSULE FORMULATION | |
| (S)—2-[p-(3-t-butylamino-2-hydroxypropoxy)phenylmethyl]-4-(2-thienyl)imidazole | 250 |
| lactose, U.S.P. | 93 |
| talc | 7 |
| OCULAR FORMULATION | |
| (S)—1-(4-bromoimidazol-2-yl)-2-{p-[3-(3,4-dimethoxyphenylethylamino)-2-hydroxypropoxy]phenyl}ethane | 15.0 |
| sodium phosphate monobasic.2H$_2$O | 6.10 |
| dibasic sodium phosphate.12H$_2$O | 16.80 |
| benzalkonium chloride | 0.10 |
| sodium hydroxide q.s. ph | 6.8 |
| water for injection q.s. ad. | 1.0 ml |
| LIQUID SUSPENSION | |
| (S)—2-{p-[3-(3,4-dimethoxyphenylethyl-amino)-2-hydroxypropoxy]phenylethyl}-4-(2-thienyl)imidazole dihydrochloride dihydrate | 5.0 |
| Veegum H.V. | 3.0 |
| methyl parable | 1.0 |
| kaolin | 10.0 |
| glycerin | 250.0 |
| water, q.s. | 1 liter |

The following examples illustrate preparation of representative imidazoles of the present invention. Unless otherwise indicated, all parts and percentages are by weight, all temperatures are in degrees Celsius, and all analyses were computed to within 0.4%.

EXAMPLE 1

(S)-2-{p-[3-(3,4-Dimethoxyphenethylamino)-2-hydroxypropoxy]phenylmethyl}-4-methylimidazole dihydrochloride (III)

Step A:
2-(p-Methoxyphenylmethyl)-4-methylimidazole (I)

A solution of chloroacetone (5.27 g, 0.057 m) in CHCl$_3$ (90 mL) was added to a stirred suspension of 4-methoxyphenylacetamidine (28.0 g, 0.17 m) in CHCl$_3$ (470 mL) over 1 hour. The mixture was heated at reflux for 75 minutes and then stirred at ambient temperature for 43 hours. The mixture was filtered and the filtrate was concentrated under reduced pressure. The oily residue was chromatographed on alumina and eluted with CHCl$_3$ to yield 8.14 g (71%) of I; m.p. 108°–109° C. (CHCl$_3$–C$_6$H$_{14}$).

Anal. Calc'd. for C$_{12}$H$_{14}$N$_2$O:C, 71.26; H, 6.98; N, 13.85. Found: C, 71.01; H, 7.07; N, 13.60.

Step B: 2-(p-Hydroxyphenylmethyl)-4-methylimidazole (II)

A mixture of 2-(p-methoxyphenylmethyl)-4-methylimidazole (5.0 g, 0.025 m), glacial acetic acid (37 mL) and 48% hydrobromic acid (125 ml) was heated at reflux for 5 hours. The solution was concentrated under reduced pressure and the oily residue was stirred in saturated sodium bicarbonate solution (55 mL) for 17 hours. The solid was collected and dried to yield 4.22 g (90%) of II; m.p. 193°–194° C. (CH$_3$CN).

Anal. Calc'd. for C$_{11}$H$_{12}$N$_2$O: C, 70.19; H, 6.43; N, 14.89. Found; C, 70.08; H, 6.60; N, 15.05

Step C:
(S)-2-{p-[3-(3,4-Dimethoxyphenethylamino)-2-hydroxypropoxy]-phenylmethyl}-4-methylimidazole dihydrochloride (III)

Sodium hydride (0.78 g, 0.0163 m, 50% dispersion in mineral oil) was added to a solution of 2-(p-hydroxybenzyl)-4-methylimidazole (3.00 g, 0.016 m) in dimethylsulfoxide (40 mL) and the mixture heated at 60° C. for 15 minutes. A solution of (S)-3-(3,4-dimethoxyphenyl)ethyl-5-(hydroxymethyl)oxazolid-2-one mesylate (5.86 g, 0.0163 m) in dimethylsulfoxide (40 mL) was added and the mixture heated at 60° C. for 3 hours. It was then poured into H$_2$O (400 mL), the pH adjusted to 10 with 40% NaOH solution and extracted with CH$_2$Cl$_2$ (3×150 mL). After washing with H$_2$O and drying, the solvent was concentrated under reduced pressure. The residue was dissolved in ethanol (100 mL), 10% NaOH solution (100 mL) added and the mixture heated at reflux under N$_2$ for 2 hours. Ethanol was evaporated under reduced pressure, H$_2$O (200 mL) was added and the mixture extracted with CH$_2$Cl$_2$ (3×150 ml). The solvent was evaporated under reduced pressure and the residue chromatographed on silica gel, eluting with 5% MeOH-CHCl$_3$ saturated with NH$_3$. The impure product was rechromatographed on silica gel and eluted with 25% ethyl acetate/25% n-butanol/25% acetic acid/25% H$_2$O. After combining and concentrating the appropriate fractions under reduced pressure, the residue was distributed between saturated sodium bicarbonate solution (50 mL) and CHCl$_3$ (100 mL), the organic layer washed with H$_2$O, dried and concentrated under reduced pressure to yield 2.68 g (39%) of oily product which was crystallized as the dihydrochloride salt III; m.p. 201.5°–203.5° C. (EtOH—Et$_2$O)

Anal. Calc'd. for C$_{24}$H$_{31}$N$_3$O$_4$.2HCl: C, 57.83; H, 6.67; N, 8.43. Found: C, 57.57; H, 6.79; N, 8.45

EXAMPLE 2

(S)-2-[p-(3-t-Butylamino-2-hydroxypropoxy)phenylmethyl]-4-(2-thienyl)imidazole dihydrogen maleate salt (IV)

Sodium hydride (0.86 g, 0.018 m, 50% dispersion in mineral oil) was added to a stirred solution of 2-(p-hydroxyphenylmethylbenzyl)-4-(2-thienyl)imidazole (4.45 g, 0.017 m) in dimethylsulfoxide (40 ml) and the mixture was heated at 60° C. for 15 minutes under nitrogen. A solution of (S)-3-t-butyl-5-(hydroxymethyl)oxazolid-2-one mesylate (4.52 g, 0.018 m) in dimethylsulfoxide (40 mL) was added and the mixture heated at 60° C. for 19 hours. After cooling, the mixture was poured into cold H$_2$O (400 mL), rendered alkaline with 40% sodium hydroxide solution and extracted with CH$_2$Cl$_2$ (3×120 mL). After washing with H$_2$O and drying over Na$_2$SO$_4$, the solvent was evaporated under reduced pressure. The residue was refluxed under N$_2$ for 71 hours in a mixture of ethanol (110 mL) and 10% sodium hydroxide solution (110 mL). Ethanol was evaporated under reduced pressure, H$_2$O (225 mL) added and the mixture extracted with CH$_2$Cl$_2$ (3×150 mL). After washing with H$_2$O and drying over Na$_2$SO$_4$, solvent was concentrated under reduced pressure. The residue was chromatographed on silica gel, eluting with 10% MeOH—CHCl$_3$ saturated with ammonia, to yield product which was crystallized as the dihydrogen maleate salt IV; m.p. at 122°–125° C. (CH$_3$OH—Et$_2$O).

Anal. Calc'd. for C$_{21}$H$_{27}$N$_3$O$_2$S.2C$_4$H$_4$O$_4$: C, 56.39; H, 5.71; N, 6.80 Found: C, 56.49; H, 6.09; N, 6.97

EXAMPLE 3

(S)-2-[p-(3-t-Butylamino-2-hydroxypropoxy)phenylmethyl]-4-methylimidazole dihydrogen maleate salt (V)

Sodium hydride (0.52 g, 0.0108 m) 50% dispersion in mineral oil) was added to a stirred solution of II (2.00 g, 0.0106 m) in dimethylsulfoxide (26 mL) and the mixture heated at 60° C. for 10 minutes under nitrogen. A solution of (S)-3-t-butyl-5-(hydroxymethyl)oxazolid-2-one mesylate (2.72 g, 0.0108 m) in dimethylsulfoxide (26 mL) was added and the mixture was heated at 60° C. for 3 hours. The mixture was cooled, poured into cold H$_2$O (260 mL), rendered alkaline with 40% sodium hydroxide solution and extracted it CH$_2$Cl$_2$ (3×80 mL). The extract was washed with H$_2$O, dried over Na$_2$SO$_4$ and concentrated under reduced pressure. The residue was heated at reflux in EtOH (75 mL) and 10% NaOH solution under nitrogen for 69.5 hours. Solvent was evaporated under reduced pressure, H$_2$O (130 mL) added to the residue and extracted with CH$_2$Cl$_2$ (3×100 mL). The combined extracts were washed with H$_2$O, dried over Na$_2$SO$_4$ and evaporated under reduced pressure. The residue was crystallized as the dihydrogen maleate salt V; m.p. 126°–129° C. (EtOH—Et$_2$O)

Anal. Calc'd. for C$_{18}$H$_{27}$N$_3$O$_2$.2C$_4$H$_4$O$_4$: C, 56.82; H, 6.42; N, 7.65 Found: C, 56.62; H, 6.58; N, 7.30

EXAMPLE 4

(S)-1-(4-Bromoimidazol-2-yl)-2-{p-[3-(3,4-dimethoxyphenyl-ethylamino)-2-hydroxypropoxy]phenyl}ethane dihydrochloride (IX)

Step A:
2-(p-Methoxyphenylethyl)-4-trifluoromethylimidazole (VI)

A mixture of 1,1-dibromo-3,3,3-trifluoroacetone (27. g, 0.1 mole) sodium acetate trihydrate (27.2 g, 0.2 mole), and water (110 mL) was stirred and heated on the steam bath for 30 minutes. The resulting solution was cooled in an ice bath and 3-(p-methoxyphenyl)propanal (16.5 g, 0.1 mole), CH$_3$OH (520 mL), and concentrated NH$_4$OH (140 mL) were added. The mixture was stirred at room temperature. After 16 hours, CH$_3$OH was stripped from the solution under reduced pressure and the solid product collected from the aqueous residue. Recrystallization of the dried solid yielded 12.53 g (46%) of VI; m.p. 146°–148° C. (EtOAc-Pet. Ether).

Analysis calc'd. for C$_{13}$H$_{13}$F$_3$N$_2$O: C, 57.78; H, 4.85; N. 10.37. Found: C, 57.72; H, 4.98; N, 10.17.

Step B:
4-Bromo-2-(p-methoxyphenylethyl)-5-trifluoromethylimidazole (VII)

N-Bromosuccinimide (5.4 g, 0.03 mole) was added to a solution of VI (8.1 g, 0.03 mole) in CH$_3$CN (150 mL) and the mixture stirred at room temperature. After 18 hours, the solution was evaporated to dryness in vacuo. The residue was partitioned between CHCl$_3$ and H$_2$O. Evaporation of the washed and dried CHCl$_3$ extract under reduced pressure left 10.5 g (quant.) of VII; m.p. 104°–106° C. (CHCl$_3$—C$_6$H$_{14}$).

Analysis calc'd. for C$_{13}$H$_{12}$BrF$_3$N$_2$O:C, 44.72; H, 3.47; N, 8.02. Found: C, 45.14; H, 3.38; N, 8.16.

Step C: 4-Bromo-2-(p-hydroxyphenylethyl)imidazole (VIII)

A solution of VII (10.5 g, 0.03 mole) in EtOH (110 mL) and 10% aq. NaOH (90 mL) was heated at reflux for 4 hours and then evaporated to dryness in vacuo. The residue was suspended in H$_2$O (120 mL), treated with conc. HCl (230 mL), and the mixture heated at reflux with stirring. After 24 hours, the mixture was cooled in an ice bath.

The precipitate was collected, dried, and chromatographed on silica gel. The product was eluted with 90CHCl$_3$—10CH$_3$OH saturated with conc. NH$_4$OH to yield 0.8 g (10%) of VIII; m.p. 191°–193° C.

Analysis calc'd. for C$_{11}$H$_{11}$BrN$_2$O: C, 49.45; H, 4.15; N, 10.49. Found: C, 49.15; H, 4.27; N, 10.40.

Step D:
(S)-1-(4-Bromoimidazol-2-yl)-2-{p-[3-(3,4-dimethoxyphenylethylamino)-2-hydroxypropoxy]phenyl}ethane dihydrochloride (IX)

Under N$_2$, sodium hydride (110 mg, 2.8 mmole, 60% oil dispersion) was added to a stirred solution of VIII (750 mg, 2.8 mmole) in dry DMSO (10 mL). The mixture was heated at 60° C. After 15 minutes when the hydrogen evolution was complete, (S)-3-(3,4-dimethoxyphenylethyl)-5-hydroxymethyloxazolid-2-one mesylate (900 mg, 2.5 mmole) was added in one portion. The resulting mixture was stirred at 65° C. for 6 hours. After cooling, the mixture was quenched in ice water (50 mL) and the gummy solid product extracted into CH$_2$Cl$_2$. Evaporation of the washed and dried CH$_2$Cl$_2$ extract left the intermediate oxazolidone derivative as a glass (1.3 g). The solid was dissolved in absolute EtOH (25 mL) and aqueous NaOH (15 ml, 10%) and the mixture heated at reflux for 3 hours. After concentration under reduced pressure, the residue was partitioned between CH$_2$Cl$_2$ and H$_2$O. The washed and dried CH$_2$Cl$_2$ extract was evaporated to dryness to yield 880 mg of the oily crude product that was purified by chromatography on silica gel, eluting with 25 EtOAc-5n-BuOH-5HOAc-3H$_2$O. The partially purified base was converted to the dihydrochloride XI to yield 77 mg (4.8%), m.p. 181°–183° C. (i-PrOH).

Analysis calc'd. for C$_{24}$H$_{30}$BrN$_3$O$_4$(+2HCl): C, 49.93; H, 5.59; N, 7.28. Found: C, 49.81; H, 5.72; N, 7.17.

EXAMPLE 5

(S)-2-{p-[3-(3,4-Dimethoxyphenylethylamino)-2-hydroxypropoxy]phenylmethyl}-4-(2-thienyl)imidazole dihydrobromide dihydrate (XII)

Step A:
2-(p-Methoxyphenylmethyl)-4-(2-thienyl)imidazole (X)

To a solution of 4-methoxyphenylacetamine (14 q, 0.085 mL) in $CHCl_3$ (200 mL) was added dropwise with stirring at room temperature a solution of (α-bromoacetyl)thiophene in $CHCl_3$ (75 mL). After 18 hours, the mixture was concentrated to dryness. The residue was chromatographed on silica gel and the product eluted with $CHCl_3$ saturated with $NH_3$ to yield 5.5 g of X (72%).

$^1$H NMR ($Me_2SO$-$d_6$) δ3.55 (3H, S), 3.8 (2H, bs), 6.6 (2H, d, J=8), 7.0 (6H, m).

Step B:
2-(p-Hydroxyphenylmethyl)-4-(2-thienyl)imidazole (XI)

A mixture of X (5.5 g, 0.02 mol), AcOH (30 mL) and 48% HBr (100 mL) was heated at reflux for 4 hours and then concentrated to dryness. The solid was stirred overnight with a solution of concentrated $NaHCO_3$ and the suspension filtered off to yield 2.7 g of XI (52%); m.p. 189°–91° C. ($H_2O$—$CH_3CN$).

Analysis calc'd for $C_{14}H_{12}N_2OS$: C, 65.60; H, 4.72; N, 10.93. Found: C, 65.62; H, 4.65; N, 10.93.

Step C:
(S)-2-{p-[3-(3,4-Dimethoxyphenylethylamino)-2-hydroxypropoxy]phenylmethyl}-4-(2-thienyl)imidazole dihydrochloride dihydrate (XII)

Prepared as described in Example 1 except the tosylate of (S)-2-phenyl-3-(3,4-dimethoxyphenylethyl)-5-(hydroxymethyl)oxazolidine was utilized instead of the mesylate of (S)-3-(3,4-dimethoxyphenylethyl)-5-(hydroxymethyl)oxazolid-2-one. The intermediate oxazolidine was hydrolyzed in 1N HCl, the reaction basified to pH>10, and extracted with $CHCl_3$ (3X). The organic extracts were dried, filtered, and concentrated to dryness. The residue was chromatographed on silica gel eluting with 2% $CH_3OH$—$CHCl_3$ saturated with $NH_3$. The product XII was crystallized as the HBr salt (5%); m.p.. 231°–233° C.

Analysis calc'd for $C_{27}H_3N_3O_4S(2HBr)$: C, 54.54; H, 6.38; N, 6.82. Found: C, 54.43; H, 6.28; N, 6.61.

EXAMPLE 6

(S)-4-Bromo-2-[p-(3-isopropylamino-2-hydroxypropoxy)phenylmethyl]imidazole (XVII)

Step A: 2-(p-Methoxyphenylmethyl)imidazole (XIII)

A mixture of p-methoxyphenylacetaldehyde (24.6 g, 0.16 mole) and 40% glyoxal in water (70 mL) was stirred in $CH_3OH$ (300 mL) and treated with concentrated $NH_4OH$ (150 mL). The resulting solution was stirred at room temperature. After 18 hours, $CH_3OH$ was stripped from the solution under reduced pressure. The residue was partitioned between $CHCl_3$ and $H_2O$, filtering from insoluble black tar. Evaporation of the washed and dried $CHCl_3$ extract under reduced pressure left the crude product (25.5 g) as an oily black solid. This was extracted with 3×600 mL of boiling $H_2O$, filtering from viscous black oil through glass wool. The combined filtrates deposited 8.0 g of slightly oily brown solid on cooling. Trituration with $CH_3CN$ yielded 6.15 g (20%) of XIII; m.p. 158°–160° C. ($CH_3CN$).

Analysis calc'd for $C_{11}H_{12}N_2O$: C, 70.19; H, 6.43; N, 14.88. Found: C, 70.00; H,, 6.38; N, 15.26.

Step B: 2-(p-Hydroxyphenylmethyl)imidazole (XIV)

A solution of XIII (6.6 g, 0.035 mole) in glacial HOAc (40 mL) and 48% HBr (110 mL) was stirred at reflux for 7 hours and then evaporated to dryness in vacuo. The residue was stirred with saturated $NaHCO_3$ (200 mL) for 16 hours at room temperature. The aqueous phase was decanted from the residue which again was stirred with saturated $NaHCO_3$ for 2 hours. This aqueous phase was decanted and the residue was extracted with 3×100 mL of boiling $H_2O$ filtering from insoluble material. All of the aqueous phases were combined and evaporated to dryness in vacuo. The residue was extracted with 3×100 mL of $CHCl_3$—MeOH (60:40), filtering from inorganic material. Evaporation of the filtrate left the crude product as an oily brown solid that was purified by chromatography on silica gel, eluting with 90$CHCl_3$—10MeOH—1$H_2O$; to yield XIV (74%); m.p. 188°–190° C. ($CH_3CN$).

Analysis calculated for $C_{10}H_{10}N_2O$: C, 68.95; H, 5.79; N, 16.08. Found: C, 68.97; H, 5.94; N, 16.21.

Step C:
(S)-2-[p-(3-Isopropyloxazolid-2-on-5-yl)methoxy]-phenylmethylimidazole (XV)

Under $N_2$, sodium hydride (1.08 g, 0.027 mole, 60% oil dispersion) was added to a stirred solution of XIV (4.25 g, 0.024 mole) in dry DMSO (60 mL). The mixture was heated to 60° C. When the hydrogen evolution was complete, a solution of (S)-3-isopropyl-5-hydroxymethyloxazolid-2-one mesylate (5.69 g, 0.024 mole) in dry DMSO (60 mL) was added dropwise. The resulting mixture was stirred at 60° C. for 3 hours, then at ambient temperature overnight. After quenching in cold water, the product was extracted into $CH_2Cl_2$. The washed and dried extract was evaporated to dryness to yield 8.54 g of the waxy crude product. This was purified by chromatography on silica gel, eluting with 95$CHCl_3$—5$CH_3OH$—0.5$H_2O$, to obtain 2.75 g (36%) of XV; m.p. 148°–151° C. (EtOAc).

Analysis calculated for $C_{17}H_{21}N_3O_3$: C, 64.74; H, 6.71; N, 13.33. Found: C, 64.41; H, 6.86; N, 13.29.

Step D:
(S)-4,5-Dibromo-2-{[p-(3-isopropyloxazolid-2-on-5-yl)methoxy]phenylmethyl}imidazole (XVI)

Compound XV (1.35 g, 4.3 mmoles) was dissolved in glacial HOAc (25 mL) and anhydrous powdered NaOAc (3.5 g, 43 mmoles) was added to give a thick stirred suspension. With cooling to 15° C., a solution of bromine (0.45 mL, 8.6 mmoles) in HOAc (10 mL) was added slowly dropwise over 1.5 hour. The resulting solution was concentrated under reduced pressure to a slush that was added to stirred ice water (400 mL). The gummy solid product was collected and dried over NaOH.

The crude dibromo compound (1.04 g, 2.2 mmoles) in dioxane (20 mL)—10% aqueous $NaHSO_3$ (50 mL) was stirred at reflux for 8 hours. After pouring the mixture into ice water (250 mL), the separated product was extracted into $CHCl_3$. The washed and dried extract was evaporated to dryness to yield 730 mg (43%) of XVI as a brown foam $^1$H NMR ($CDCl_3$) δ1.2 (6H, d), 3.7 (2H, s), 3.8 (7H, m), 6.8 (5H, m); IR (neat) 5.8μ (C=O).

Step E:
(S)-4-Bromo-2-[p-(3-isopropylamino-2-hydroxypropoxy)phenylmethyl]imidazole (XVII)

A solution of XVI (700 mg, 1.8 mmoles) in EtOH (10 mL)—10% aqueous NaOH (10 mL) was stirred at reflux for 7 hours. After removal of the EtOH in vacuo, the residue was diluted with water and extracted with $CHCl_3$. The washed and dried $CHCl_3$ extract was evaporated to dryness to yield 250 mg of the crude product as a viscous yellow oil. This was purified by chromatography on silica gel, eluting with $95CHCl_3$—$5CH_3OH$ saturated with concentrated $NH_4OH$. Trituration of the purified product afforded 215 mg (32%) of XVII; m.p. 125°–127° C. ($Et_2O$).

Analysis calculated for $C_{16}H_{22}BrN_3O_2$: C, 52.18; H, 6.02; N, 11.41. Found: C, 52.38; H, 6.14; N, 11.06.

EXAMPLE 7

(S)-1-[4-(2-Thienyl)imidazol-2-yl]-2-p-[3-(3,4-dimethoxy-phenylethylamino)-2-hydroxypropoxy]phenyl ethane dihydrochloride dihydrate (XXI)

Step A: 3-(p-Methoxyphenyl)propionamidine hydrochloride (XVIII)

Under $N_2$, a stirred solution of 3-(p-methoxyphenyl)propionitrile (11.2 g, 0.069 mole) in $CH_3OH$ (3 mL)-ether (5 mL)-dioxane (5 mL) was cooled in an ice bath while gaseous HCl was introduced until 4 g had been absorbed. The resulting mixture was held in a refrigerator. After 2 days, the solid mass was suspended in ether and the hygroscopic solid was collected and transferred quickly into a solution of ammonia (22 g) in $CH_3OH$ (100 mL) cooled to $-78°$ C. The stirred mixture was allowed to warm to room temperature. After 24 hours, the solution was evaporated to dryness under reduced pressure. The solid residue was triturated with ether and collected to yield 11.8 g (79%) of XVIII; m.p. 123°–129° C. A sample triturated with acetone melted at 131°–133° C.

Anal. calc'd for $C_{10}H_{14}N_2O(+HCl)$: C, 55.94; H, 7.04; N, 13.05. Found: C, 55.20; H, 7.22; N, 13.05.

Step B:
2-(p-Methoxyphenylethyl)-4-(2-thienyl)imidazole (XIX)

Prepared as described in Example 5 for compound X except that XVIII was used in place of 4-methoxyphenylacetamidine. The crude product was purified by chromatography on silica gel, eluting with 2% $CH_3OH$—$CHCl_3$; yield, 50% of XIX, 'H NMR ($CDCl_3$) δ2.9 (4H, s), 3.7 (3H, s), 6.9 (8H, m).

Step C:
2-(p-Hydroxyphenylethyl)-4-(2-thienyl)imidazole (XX)

A mixture of XIX (2.9 g, 0.01 mole), glacial HOAc (10 mL) and 48% HBr (35 mL) was stirred at reflux for 3 hours. The hot solution was decanted from the separated tar and chilled at 5°–10° C. overnight. The precipitated hydrobromide salt was collected, washed with $Et_2O$, dissolved in $H_2O$ (100 mL), and the solution was made basic with saturated $NaHCO_3$ solution. The solid was collected, chromatographed on silica gel, and the product eluted with $95CHCl_3$—$5CH_3OH$—$0.5H_2O$ to yield 0.725 g (27%) of XX; m.p. 165.5°–167° C. (50% $CH_3OH$).

Analysis calculated for $C_{15}H_{14}N_2OS$: C, 66.64; H, 5.22; N, 10.36. Found: C, 66.16; H, 5.20; N, 10.26.

Step D:
(S)-1-[4-(2-Thienyl)imidazol-2-yl]-2-{p-[3-(3,4-dimethoxyphenylethylamino)-2-hydroxypropoxy]-phenyl}ethane dihydrochloride dihydrate (XXI)

Prepared as described previously in Example 4, except XX was used in place of VIII; 14% yield; m.p. 115°–120° C. (EtOH).

Analysis calculated for $C_{28}H_{33}N_3O_4S(+2HCl+2H_2O)$: C, 54.54; H, 6.38; N, 6.82. Found: C, 54.43; H, 6.28; N, 6.61.

EXAMPLE 8

(S)-2-{p-[3-(3,4-Dimethoxyphenylethylamino)-2-hydroxypropoxy]phenylmethyl}-4-acetylimidazole.hydrochloride (XXVIII)

Step A: p-Methoxyphenylmethylamidoxime (XXII)

A mixture of $H_2NOH.HCl$ (74.7 g, 1.08 mol), $K_2CO_3$ (60.1 g, 0.43 mol), p-methoxybenzylacetonitrile (64 g, 0.43 mol), EtOH (450 mL), and $H_2O$ (450 mL) was heated at 60°–70° C. with stirring. After 24 hours, the EtOH was removed under reduced pressure (20 mm) and the suspension filtered off to yield 50 g of XXII (65%); m.p. 108°–109° C. ($C_6H_5CH_3$).

Analysis calculated for $C_9H_{12}N_2O_2$: C, 59.98; H, 6.71; N, 15.54. Found: C, 59.99; H, 7.04; N, 15.50.

Step B:
4-Carboethoxy-2-(4-methoxyphenylmethyl)imidazole (XXIII)

A mixture of ethyl propiolate (20 g, 0.2 mol), XXII (36.7 g, 0.2 mol) and absolute EtOH (600 mL) was heated at reflux with stirring. After 18 hours, the reaction mixture was concentrated to dryness, the residue treated with diphenylether (200 mL), and the mixture heated at 180°–200° with stirring. After ½ hour, the brown-black reaction was cooled to 110° and poured into Pet-ether (2 L) with stirring. The solid was filtered off, the residue dissolved in $CHCl_3$ and chromatographed on alumina of activity grade II. The product was eluted with 15% Pet ether-$CHCl_3$ to yield 5.6 g (43%) of XXIII; m.p. 119°–21° C. ($CH_3CN$).

Analysis calculated for $C_{14}H_{16}N_2O_3$. C, 64.60; H, 6.20; N, 10.76. Found: C, 64.79; H, 6.19; N, 11.05.

Step C:
4-Carbamoyl-2-(4-methoxybenzylmethyl)imidazole (XXIV)

A mixture of XXIII (9.2 g, 0.035 mol), $CH_3OH$ (300 mL) and $NH_3$ (100 g) was heated in a sealed tube at 120° C. After 24 hours, the contents were removed and the mixture concentrated to dryness. The residue was triturated with $Et_2O$ to yield 7.9 g (97%) of XXIV; m.p. 218°–19° C. ($CH_3CN$).

Analysis calculated for $C_{12}H_{13}N_3O_2$: C, 62.32; H, 5.66; N, 18.17. Found: C, 62.15; H, 5.90; N, 17.99.

Step D: 4-Cyano-2-(4-methoxyphenylmethyl)imidazole (XXV)

A mixture of XXIV (7.0 g, 0.031 mol) and $POCl_3$ (100 mL) was heated at reflux with stirring. After 6 hours, the reaction was stirred at room temperature overnight, concentrated to dryness, the residue flushed with toluene, treated with saturated $Na_2CO_3$, extracted with 20% $CH_3OH$—$CHCl_3$ (2X) and $CHCl_3$ (2X). The combined organic extracts were backwashed with saturated NaCl, dried, filtered and concentrated to dryness. The residue was triturated with Et$_2$O to yield 4.9 g (77%) of XXV; m.p. 170°-1° C. (CH$_3$CN).

Analysis calculated for C$_{12}$H$_{11}$N$_3$O; high resolution MS 213.0903.

Step E: 4-Acetyl-2-(4-Methoxyphenylmethyl)imidazole (XXVI)

To a solution of XXV (2.11 g, 0.01 mol) in THF (50 mL) was added with stirring at room temperature methyl magnesium chloride (12 mL, 2.8M, 0.034 mol) in THF. After 24 hours, 3N HCl (50 mL) was added dropwise with stirring and the resulting mixture heated at reflux for 20 minutes. After cooling to room temperature, the solution was neutralized with solid Na$_2$CO$_3$ and extracted with CHCl$_3$ (3X). The organic extracts were dried, filtered and concentrated to dryness to yield 2.35 g (100%) of XXVI; m.p. 147°-48° C. (CH$_3$CN).

Analysis calculated for C$_{13}$H$_{14}$N$_2$O$_2$: C, 67.80; H, 6.13; N, 12.17. Found: C, 67.67; H, 6.28; N, 12.28.

Step F: 4-Acetyl-2-(4-hydroxyphenylmethyl)imidazole (XXVII)

A solution of XXVI (2.2 g, 0.01 mol), AcOH (10 mL) and 48% HBr (40 mL) was heated at reflux. After 24 hours, the solution was concentrated to dryness, neutralized with NaHCO$_3$ to pH 8.5 and the mixture stirred at room temperature. The suspension was concentrated to dryness mixed with CH$_3$OH (100 mL) and silica gel (20 g) and concentrated to dryness. The solid was placed on a silica gel column and the product eluted with 5% CH$_3$OH—CHCl$_3$ to yield 1.7 g (81%) of XXVII; m.p. 229°-31° C. (CH$_3$CN).

Analysis calculated for C$_{12}$H$_{12}$N$_2$O$_2$: C, 66.65; H, 5.60; N, 12.96. Found: C, 66.67; H, 5.70; N, 13.31.

Step G: (S)-2-p-[3,4-Dimethoxyphenylethylamino)-2-hydroxypropoxy]phenylmethyl-4-acetylimidazole hydrochloride (XXVIII)

Compound XXVIII was prepared as described in Example 4 except XXVII was used in place of VIII. The compound was chromatographed on silica gel and the product eluted with 10% CH$_3$OH—CHCl$_3$ to yield 75 mg of XXVIII (2.4%); m.p. 191°-3° C. (CH$_3$CN).

Analysis calculated for C$_{25}$H$_{31}$, N$_3$O$_5$.HCl (HCl came from CHCl$_3$): C, 61.28; H, 6.58; N, 8.58. Found: C, 60.96; H, 6.76; N, 8.34.

EXAMPLE 9

(S) 3-[3,4-Dimethoxyphenylethylamino]-2-hydroxy-1-[4-[2-imidazolylmethoxymethyl]phenoxy]propane (XXXII)

Step A: 2-Carbomethoxy-1-tritylimidazole (XXIX)

Compound XXIX was prepared as described for the preparation of 3-carboethoxy-1-tritylimidazole by Kirk (J. Org. Chem., (1978) 43, 4381); 23% yield; m.p. 186°-8° C. (EtOH).

Analysis calculated for C$_{24}$H$_{20}$N$_2$O: N, 7.6; C, 78.27; H, 5.47 Found: N, 7.95; C, 77.96; H, 5.52.

Step B: 2-Hydroxymethyl-1-tritylimidazole (XXX)

A solution of XXIX (1.1 g, 0.003 mol) in dry THF (10 mL) was added dropwise with stirring at 0°-4° C. to a suspension of LAH (0.14 g, 0.0036 mol) in dry THF (10 mL). The mixture was stirred at room temperature, further cooled, H$_2$O (0.13 mL) added, followed by 10% NaOH (0.2 mL) and finally H$_2$O (0.33 mL). The mixture was stirred at room temperature for 30 minutes, then at 0° C. for 1 hour, filtered and the collected solid, washed with THF, hot EtOH (2x) and CHCl$_3$. The combined filtrates were concentrated to dryness. The residue was triturated with hot absolute EtOH to yield 0.7 g (69%) of XXX; m.p. 243°-4°.

Analysis calculated for C$_{23}$H$_{20}$N$_2$·½H$_2$O: C, 79.06; H, 6.06; N, 8.02 Found: C, 79.16; H, 5.88; N, 8.26

Step C: (S) 3-(3,4-Dimethoxyphenylethyl)-5-(4-hydroxymethylphenoxymethyl)-oxazoline-2-one (XXXI)

To a stirred solution of 4-hydroxybenzyl-alcohol (4.1 g, 0.0033 mol) in DMSO (75 mL), NaH (60%) oil dispersion, 1.32 g, 0.0033 mol) was added under N$_2$. The mixture was heated at 60° C. for 15 minutes and then (S)-3-(3,4-dimethoxyphenyl)ethyl-5-(hydroxymethyl-)oxazolid-2-one mesylate (10.8 g, 0.003 mol) was added. The mixture was stirred at 60° C. for 2 hours, then poured in H$_2$O and the aqueous extracted with EtOAc (2X). The organic extracts were washed with saturated Na$_2$CO$_3$, 0.1N HCl, H$_2$O, filtered and concentrated to dryness. The residue was chromatographed on silica gel eluting with CHCl$_3$–CH$_3$OH—H$_2$O (90:5:0.5) to yield 5.0 g (43%) of XXXI.

Analysis calculated for C$_{21}$H$_{25}$NO$_6$.½H$_2$O: N, 3.53; C, 63.62; H, 6.61 Found: N, 3.45; C, 63.62; H, 6.46.

Step D: (S) 3-[3,4-Dimethoxyphenylethylamino]-2-hydroxy-1-[4-[2-imidazolylmethoxymethyl]phenoxy]propane (XXXII)

Compound XXXI (2.71 g, 0.007 mL) was dissolved in CH$_2$Cl$_2$ (25 mL), cooled and Et$_3$N (0.78 g, 0.0077 mol) added. To the cooled solution, methanesulfonyl chloride (0.88 g, 0.0077 mol) in CH$_2$Cl$_2$ (2 mL) was added and stirred at room temperature. After 3 hours another portion of methanesulfonylchloride (0.09 g, 0.007 mol) was added. After 1 hour, the reaction was poured in H$_2$O (25 mL) containing K$_2$CO$_3$ (1 g) and the organic extracted with CH$_2$Cl$_2$ (3X). The aqueous extracts were washed with H$_2$O, 0.5N, HCl, H$_2$O, dried, filtered and concentrated to dryness. The residue was dissolved in dry DMSO (20 mL) and added with stirring at room temperature to a solution of XXX (1.7 g, 0.005 mol) and NaH (60% oil dispersion, 0.22 g, 0.0055 mol) in DMSO (20 mL). After 2 hours, another portion of NaH (0.2 g) was added and stirred at room temperature for an additional 2 hours. The solution was then poured in H$_2$O and the aqueous extracted with EtOAc (2X). The organic extracts were dried, filtered and concentrated to dryness. The residue was treated with CH$_3$OH (25 mL) and 40% NaOH (6 mL) and the solution heated at reflux. After 2 hours, the solution was poured into H$_2$O. The aqueous layer was extracted with CHCl$_3$ (3X) and the organic extracts dried, filtered and concentrated to dryness. The residue was treated with CH$_3$OH (50 mL) and HOAc (2.5 mL) and heated at reflux for 2 hours. The reaction was then concentrated to dryness, 0.1N HCl (75 mL) added, the aqueous extracted with CHCl$_3$ (3X) and the organic extracts discarded. The aqueous solution was basified to pH 10 with saturated Na$_2$CO$_3$ and extracted with CHCl$_3$ (2X). The organic extracts were dried, filtered and concentrated to dryness. The residue was chromatographed on silica gel eluting with CHCl₃ saturated with NH₃ and CHCl₃—CH₃OH—NH₄OH (70:5:0.5 to 90:10:1) to yield XXXII; 13% yield.

Analysis calculated for $C_{24}H_{31}N_3O_5$: N, 9.52; C, 65.29; H, 7.08. Found: N, 8.94; C, 64.95; H, 6.94.

EXAMPLE 10

(S) 3-(3,4-Dimethoxyphenylethylamino)-2-hydroxy-1-[4-(2-imidazolylmethoxy)phenoxy]propane (XXXV)

Step A: 3-(3,4-Dimethoxyphenylethyl)-5-(4-hydroxyphenoxymethyl)oxazolid-2-one (XXXIII)

To a solution of 4-benzyloxyphenol (6.6 g, 0.0033 mol) in DMSO (75 mL) was added under N₂ with stirring NaH (60% oil dispersion, 1.32 g, 0.0033 mmol). The mixture was stirred for 15 minutes and then (S)-3-(3,4-dimethoxyphenyl)ethyl-5-(hydroxymethyl)oxazolid-2-one mesylate (10.78 g, 0.003 mol) added. The mixture was heated at 60° C. for 1 hour and then the DMSO was removed under reduced pressure (2 mm). The residue was partitioned between H₂O and EtOAc (3X). The organic extracts were washed with dilute Na₂CO₃, 0.2N HCl, H₂O, dried, filtered and cooled to yield 14.5 g of crude product. The alcohol (4.63 g, 0.001 mol) was suspended in 4.4% HCO₂H in CH₃OH (100 mL) under N₂, 10% Pd on C (0.93 g) added and the mixture stirred at room temperature overnight. The suspension was filtered and the filtrate evaporated to dryness to yield 1.7 g (96%) of XXXIII; ¹H NMR (CDCl₃) δ 2.8 (2H, t, J=7), 3.45 (4H, m), 3.77 (3H, s), 3.8 (3H, s), 3.85 (2H, d), 4.7 (1H, m), 6.75 (7H, m).

Step B: (S) 5-[4-[2-(1-Benzyl)imidazolylmethyloxy]phenoxymethyl]-3-(3,4-dimethoxyphenylethyl)oxazoline-2-one (XXXIV)

Compound XXXIII (1.4 g, 0.00375 mol) was dissolved in dry DMSO (15 mL) and NaH (60% oil dispersion, 0.3 g, 0.0075 mol) added with stirring. After 15 minutes, 1-benzyl-2-chloromethylimidazole (0.91 g, 0.0025 mol) was added and the mixture stirred at room temperature for 4 hours. The reaction mixture was poured in H₂O and the aqueous extracted with EtOAc (2X). The organic extracts were dried, filtered and concentrated to dryness. The residue was chromatographed on silica gel eluting with CHCl₃—CH₃OH—H₂O (80:20:2) to yield 0.84 g (41%) of XXXIV. ¹H NMR (CDCl₃) 2.8 (2H, t, J=7), 3.50 (4H, m), 3.77 (3H, s), 3.8 (3H, s), 3.9 (2H, d), 4.7 (1H, m), 5.0 (2H, s), 5.2 (2H, s), 6.7–7.4 (14H, m).

Step C: (S) 3-(3,4-Dimethoxyphenylethyl)-2-hydroxy-1-[4-(2-imidazolylmethoxy)phenoxy]propane (XXXV)

Compound XXXIV (0.82 g, 0.0015 mol) was treated with CH₃OH (25 mL) and 40% NaOH (6 mL) and the mixture heated at reflux for 3 hours. The reaction was poured into H₂O and extracted with CHCl₃ (2X). The organic extracts were washed with H₂O, dried, filtered and concentrated to dryness. The residue (0.62 g, 0.0012 mol) was suspended in liquid NH₃ (20 mL) and Na (0.17 g, 0.006 mol) added. After the solution turned blue, the mixture was stirred for 15 minutes and then solid NH₄Cl (0.55 g) added, NH₃ was allowed to evaporate, H₂O was added and the pH adjusted to 1 by the addition of concentrated HCl (~0.3 mL). The aqueous solution was extracted with CHCl₃ (2X), adjusted to pH>10 with saturated Na₂CO₃. The aqueous solution was extracted with CHCl₃ (2X), the organic extracts dried, filtered and concentrated to dryness. The crude product was chromatographed on silica gel using a linear gradient elution with CHCl₃ (1 liter) and CHCl₃—CH₃OH—H₂O (60:40:4) containing 2.5 mL of concentrated NH₄OH to yield XXXV; 25% yield, m.p. 129°–30° C. (trituration with CH₃CN—Et₂O).

Analysis calculated for $C_{23}H_{29}N_3O_5$: N, 9.83; C, 64.62; H, 6.84. Found: N, 9.61; C, 64.54; H, 6.70

Using the procedures and methods described in the foregoing Methods and Examples additional compounds of Formula I can be prepared as set forth in Table I below wherein Ph denotes phenyl and DMPE denotes 3,4-dimethoxyphenylethyl:

TABLE I

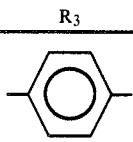

| | R | R₁ | R₂ | m | X | n | R₃ | R₄ | R₅ |
|---|---|---|---|---|---|---|---|---|---|
| (a) | H | H | H | 1 | O | 1 |  | OH | DMPE |
| (b) | " | " | " | " | CH₂ | 0 | " | " | " |
| (c) | " | Br | " | 0 | " | " | " | " | C₆H₅ |
| (d) | " | " | " | 1 | " | " | " | " | CH₂CH₂CH₃ |
| (e) | " | O‖CH₃C— | " | " | " | " | 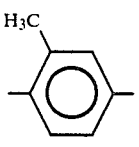 H₃C | " | DMPE |
| (f) | " | Br | " | 2 | " | " |  | " | " |

TABLE I-continued $$\underset{R_2}{\overset{R}{\underset{R_1}{\diagdown}}}\!\!\!\diagup\!\!\!\overset{N}{\underset{N}{\diagdown}}\!\!-(CH_2)_m-X-(CH_2)_n-R_3-O-CH_2-\overset{R_4}{\underset{}{C}}H-CH_2-NHR_5 \qquad I$$

| | R | $R_1$ | $R_2$ | m | X | n | $R_3$ | $R_4$ | $R_5$ |
|---|---|---|---|---|---|---|---|---|---|
| (g) | " | $C_2H_5\overset{O}{\underset{\|}{C}}-$ | " | 0 | $CH_2$ | " | " | " | $(CH_3)_2CH-$ |
| (h) | " | $H_3COCH_2$ | " | " | " | " | ![2,4-disubst phenyl with O=C-CH3] | " | DMPE |
| (i) | " | Br | $CH_3$ | " | " | " | ![1,4-phenylene] | " | $-(CH_2)_2$-Ph |
| (j) | " | CN | H | 2 | O | 1 | " | " | $-(CH_2)_2NH\overset{O}{\underset{\|}{C}}NH-Ph$ |
| (k) | $CH_3$ | $CH_3\overset{O}{\underset{\|}{C}}-$ | " | 1 | " | 0 | ![phenylene with CN] | " | $(CH_3)_3C-$ |
| (l) | Br | Br | H | 0 | $CH_2$ | 0 | ![1,4-phenylene] | OH | $-(CH_2)_2$-C6H4-OCH3 |
| (m) | H | ![3,4-dichlorophenyl] | " | 3 | " | " | ![phenylene-Cl] | " | cyclopropyl $-CH\underset{CH_2}{\overset{CH_2}{\diagup\!\!\!\diagdown}}$ |
| (n) | " | ![pyrazinyl] | " | 0 | " | 0 | ![phenylene-CH3] | " | DMPE |
| (o) | " | $CO_2H$ | " | " | " | " | ![phenylene] | " | cyclopropyl $-CH\underset{CH_2}{\overset{CH_2}{\diagup\!\!\!\diagdown}}$ |
| (p) | " | $CO_2Et$ | " | 2 | O | 2 | " | $C_6H_5\overset{O}{\underset{\|}{C}}-$ | DMPE |
| (q) | " | $CH(CH_3)_2$ | " | " | S | " | " | OH | $(CH_2)_2OCH_2CH_3$ |
| (r) | " | $C(CH_3)_3$ | " | 1 | O | " | ![phenyl-O-vinyl] | " | |

TABLE I-continued $$\underset{R_1}{\overset{R}{>}}\!\!=\!\!\underset{\underset{R_2}{|}}{N}\!\!-\!\!C(=N-)-(CH_2)_m-X-(CH_2)_n-R_3-O-CH_2-\underset{R_4}{CH}-CH_2-NHR_5 \quad I$$

| | R | R₁ | R₂ | m | X | n | R₃ | R₄ | R₅ |
|---|---|---|---|---|---|---|---|---|---|
| (s) | " | 3-pyridyl | " | 2 | " | 0 | 1,4-phenylene | " | DMPE |
| (t) | " | H₂NC(=O)– | " | " | " | " | 1,4-phenylene | " | " |
| (u) | " | (CH₃)₂NC(=O)– | " | 1 | " | " | 1,4-phenylene | " | " |
| (v) | " | 2-thienyl | " | 0 | CH₂ | 0 | 2,3-phenylene | " | " |
| (w) | " | Br | " | 1 | " | " | 1,4-phenylene | " | CH₂CH₂-(4-pyrimidinyl) |
| (x) | " | H | " | 0 | " | " | " | " | CH₂CH₂-(4-hydroxyphenyl) |
| (y) | " | CH₃ | " | " | " | " | " | " | CH₂CH₂-(4-chlorophenyl) |
| (z) | CH₃ | " | " | " | " | " | " | " | CH₂CH₂-(4-hydroxy-3-methylphenyl) |
| (aa) | H | " | " | " | " | " | " | " | CH₂CH₂SCH₂CH₃ |
| (bb) | H | 2-furyl | H | 2 | CH₂ | 2 | 1,4-phenylene | OH | (CH₃)₂CH– |
| (cc) | " | 4-pyridyl | " | " | " | 1 | " | " | –CH(–CH₂–CH₂–) (cyclopropyl) |
| (dd) | " | phenyl | " | 3 | O | " | 3-methoxy-1,4-phenylene | (CH₃)₃C–C(=O)– | DMPE |

TABLE I-continued $$R\underset{R_1}{\overset{N}{=}}\underset{\underset{R_2}{|}}{N}-(CH_2)_m-X-(CH_2)_n-R_3-O-CH_2-\underset{\underset{R_4}{|}}{CH}-CH_2-NHR_5 \qquad I$$

| | R | R₁ | R₂ | m | X | n | R₃ | R₄ | R₅ |
|---|---|---|---|---|---|---|---|---|---|
| (ee) | " | CF₃ | " | " | " | 0 | 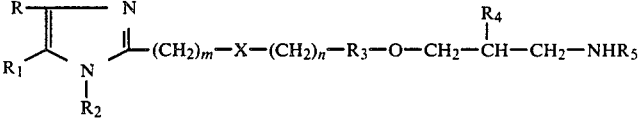 | OH | (CH₃)₂CH— |
| (ff) | " | CH₃\N—CH₂ / CH₃ | CH₃ | " | S | 1 | " | " | DMPE |
| (gg) | " | Cl | H | 2 | " | 2 | " | " | (CH₂)₂NHC(=O)NH—n-butyl |
| (hh) | Cl | CH₃ | " | " | 1 | CH₂ | 1 | " | " | —(CH₂)₂—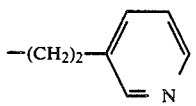 |
| (ii) | H | " | " | " | " | 0 | " | " | CH₂CH₂NHC(=O)—NH₂ |

In evaluating the β-blocking effectiveness of the present compounds, it was noted that the compounds exhibit cardioselectivity; that is, the compounds are more effective in reducing the heart rate effects of isoproterenol than they are in blocking the isoproterenol effects on the bronchi. Expressed in different terms, a smaller amount of a compound of the invention is required to block isoproterenol-induced elevation in heart rate than is required to block the isoproterenol-induced relaxation of the bronchi. This cardioselectivity factor can be expressed as the ratio of $ED_{50}$ for pulmonary effect $(\beta_2):ED_{50}$ for cardiac effect $(\beta_1)$. Where the $\beta_2:\beta_1$ ratio is over 1, then the compound would be considered to have cardioselective activity.

Compounds of the invention which were tested and found to have $\beta_2:\beta_1$ ratios greater than 1 are shown in Table II below wherein the in vitro results obtained were determined according to the procedure described by Baldwin et al., *J. Med. Chem.*, 26, 956–7 (1983):

TABLE II

Compounds Having $B_2:B_1 > 1$

| Example | Compound | $B_2:B_1$ |
|---|---|---|
| 1 | (S)—2-{p-[3-(3,4-dimethoxyphenethyl-amino)-2-hydroxypropoxy]phenylmethyl}-4-methylimidazole | 144 |
| 2 | (S)—2-[p-(3-t-butylamino-2-hydroxy-propoxy)phenylmethyl]-4-(2-thienyl)-imidazole dihydrogen maleate salt | 10.5 |
| 3 | (S)—2-[p-(3-t-butylamino-2-hydroxy-propoxy)phenylmethyl]-4-methylimidazole | 3.3 |
| 4 | (S)—1-(4-bromoimidazol-2-yl)-2-{p-[3-(3,4-dimethoxyphenylethylamino)-2-hydroxy-propoxy]phenyl}ethane | 398 |
| 5 | (S)—2-{p-[3-(3,4-dimethoxyphenylethyl)-amino)-2-hydroxypropoxy]phenylmethyl}-4-(2-thienyl)imidazole | >10,000 |
| 6 | (S)—4-bromo-2-[p-(3-isopropylamino-2-hydroxypropoxy)phenylmethyl]imidazole | 7.8 |
| 7 | (S)—1-[4-(2-thienyl)imidazol-2-yl]-2-{p-[3-(3,4-dimethoxyphenylethylamino)-2-hydroxy-propoxy]phenyl}ethane | 1280 |
| 8 | (S)—2-{p-[3-(3,4-dimethoxyphenylethyl-amino)-2-hydroxypropoxy]phenylmethyl}-4-acetylimidazole | >9333 |
| 9 | (S)—3-[3,4-dimethoxyphenylethyl-amino]-2-hydroxy-1-[4-[2-imidazolyl-methoxymethyl]phenoxy]propane | 302 |
| 10 | (S)—3-(3,4-dimethoxyphenylethyl-amino)-2-hydroxy-1-[4-(2-imidazolyl-methoxy)phenoxy]propane | 209 |

As previously mentioned, the β-adrenergic blocking agents of the invention are devoid of intrinsic sympathomimetic activity (ISA); i.e., they are devoid of partial agonism causing a greater slowing of heart rate than β-blockers with partial agonism. Compounds which exhibit this feature should be more efficacious in the treatment of angina, a condition responsive to agents with decreased oxygen consumption. Since bradycardia (slowing of heart rate) is a major determinant of oxygen consumption, β-blockers that exhibit ISA should produce less of a decrement in oxygen consumption and also cause a sharp decline in blood pressure due to stimulation of vascular $\beta_2$-receptors which subserve vasodilation. Thus, β-blocking agents which are devoid of ISA would be expected to produce a more gradual decline in blood pressure.

Compounds of the invention were tested for ISA using the following method:

Male Sprague-Dawley rats weighing 250 to 350 grams were pretreated with reserpine, 5 mg/kg i.p., approximately 18 hours prior to the experiment. Dial-Urethane at 1 mg/kg i.p. was used for anesthesia. The vagi were cut and a tracheal tube was inserted. Blood pressure was recorded from an indwelling arterial (carotid artery) catheter and the heart rate was calculated from the blood pressure tracing. Mean arterial pressure and heart rate were recorded at 0, 2, 4, 8, 15, 30, 45 and 60 minutes. Compounds were dissolved in distilled H$_2$O or 1N HCl and administered intravenously over two minutes. For compounds producing bell-shaped curves, only the ascending segment of the dose response was used to calculate ED$_{50}$'s.

The results of these tests are listed below in Table III wherein "+" indicates the compounds tested were devoid of ISA and "−" means the compounds tested exhibited ISA.

TABLE III

| Compound of Example | ISA |
|---|---|
| 1 | + |
| 5 | + |
| 6 | + |
| 7 | + |
| 8 | + |

What is claimed is:

1. A compound having the formula:

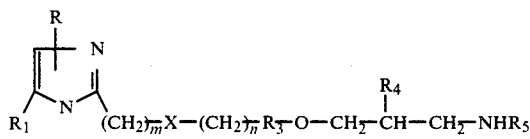

R and R$_1$ are independently:
hydrogen;
C$_1$-C$_8$ linear or branched alkyl;
fluoro, bromo, chloro;
heteroaryl groups having 5-ring atoms selected from furyl, thienyl and N—C$_1$-C$_8$-lower alkylpyrrolyl;
carboalkoxy wherein the alkyl group has up to 8 carbon atoms;
CF$_3$;
carbamoyl;
cyano;

wherein R$_a$ is hydrogen or C$_1$-C$_8$ alkyl;
unsubstituted or substituted aryl of C$_6$ having 1-5 substituents selected from fluoro, bromo, chloro, C$_1$-C$_8$ linear or branched alkly, or C$_1$-C$_8$ alkoxy;
heteroaryl groups having 6-ring atoms selected from pyridyl, pyrazinyl, pyrimidinyl, pyridazinyl;
R$_2$ is hydrogen; C$_1$-C$_8$ linear or branched alkyl;
R$_3$ is unsubstituted or substituted arylene of C$_6$ or C$_{10}$ having 1-2 substituents selected from halo, C$_1$-C$_8$ alkoxy, alkenyloxy having up to 8 carbon atoms;
C$_1$-C$_8$ linear or branched alkyl;
cyano,

wherein R$_a$ is as defined above;
R$_4$ is hydroxy;
R$_5$ is C$_3$-C$_5$ cycloalkyl;
C$_1$-C$_8$ linear or branched alkyl;
unsubstituted or substituted aralkyl wherein the alkyl is linear or branched C$_1$-C$_8$ and the aryl is C$_6$-C$_{10}$ having 1-2 substituents selected from C$_1$-C$_8$ alkoxy, hydroxy, fluoro, bromo, chloro, C$_1$-C$_8$ alkyl;
heteroaryl having 6-ring atoms containing 1-2N heteroatoms;
X is oxygen or CH$_2$; and,
m an n are independently 0-2 provided that at least one of m or n is 1.

2. A compound of claim 1 wherein:
R and R$_1$ are independently:
hydrogen;
C$_1$-C$_8$ linear or branched alkyl;
fluoro, bromo, chloro;
heteroaryl groups having 5-ring atoms selected from furyl, thienyl and N—C$_1$-C$_8$ lower alkylpyrrolyl;
carboalkoxy wherein the alkyl group has up to 8 carbon atoms;
CF$_3$;

wherein R$_a$ is C$_1$-C$_3$ alkyl;
R$_2$ is hydrogen;
R$_3$ is 1,4-phenylene;
R$_4$ is hydroxy;
R$_5$ is C$_3$-C$_5$ cycloalkyl;
C$_1$-C$_8$ linear or branched alkyl;
unsubstituted or substituted aralkyl wherein the alkyl is linear or branched C$_1$-C$_8$ and the aryl is C$_6$ having 1-2 C$_1$-C$_8$ alkoxy substituents;
X is CH$_2$; and,
m and n are independently zero or 1.

3. A compound according to claim 1 which is (S)-2-p-[3-(3,4-dimethoxyphenylethylamino)-2-hydroxypropoxy]phenylmethyl-4-methylimidazole.

4. A compound according to claim 1 which is (S)-2-[p-(3-t-butylamino-2-hydroxypropoxy)phenyl-methyl]-4-(2-thienyl)imidazole.

5. A compound according to claim 1 which is (S)-2-[p-(3-t-butylamino-2-hydroxypropoxy)phenyl-methyl]-4-methylimidazole.

6. A compound according to claim 1 which is (S)-1-(4-bromoimidazol]-2-yl)-2-p-[3-(3,4-dimethoxyphenylethylamino)-2-hydroxypropoxy]phenyl ethane.

7. A compound according to claim 1 which is (S)-2-p-[3-(3,4-dimethoxyphenylethamino)-2-hydroxypropoxy]phenylmethyl-4-(2-thienyl)-imidazole.

8. A compound according to claim 1 which is (S)-4-bromo-2-[p-(3-isopropylamino-2-hydroxypropoxy)-phenylmethyl]imidazole.

9. A compound according to claim 1 which is (S)-1-[4-(2-thienyl)imidazol-2-yl]-2-p-[3-(3,4-dimethoxyphenylethylamino)-2-hydroxypropoxy]phenyl ethane.

10. A compound according to claim 1 which is (S)-2-p-[3-(3,4-dimethoxyphenethylamino)-2-hydroxypropoxy]phenylmethyl-4-acetylimidazole.

11. A compound according to claim 1 which is (S)-3-[3,4-dimethoxyphenylethylamino]-2-hydroxy-1-[4-[2-imidazolylmethoxymethyl]phenoxy propane.

12. A compound according to claim 1 which is (S)-3-(3,4-dimethoxyphenylethylamino)-2-hydroxy-1-[4-(2-imidazolylmethoxy)phenoxy]propane.

* * * * *